United States Patent [19]
Balogh et al.

[11] Patent Number: 6,149,215
[45] Date of Patent: Nov. 21, 2000

[54] DURABLE SLINGS FOR VEHICLE FRAME TURNOVER MACHINES AND METHOD OF MAKING THE SLINGS

[75] Inventors: Dennis J. Balogh; William D. Murlick, both of Westland, Mich.

[73] Assignee: DP Brown of Detroit Incorporated, Westland, Mich.

[21] Appl. No.: 09/348,087

[22] Filed: Jul. 6, 1999

Related U.S. Application Data

[60] Provisional application No. 60/091,949, Jul. 7, 1998.

[51] Int. Cl.[7] ........................................................ B66C 1/12
[52] U.S. Cl. .............................................................. 294/74
[58] Field of Search ................................ 294/74; 57/210, 57/211, 223, 235, 241, 258

[56] References Cited

U.S. PATENT DOCUMENTS

| | | | |
|---|---|---|---|
| 3,290,083 | 12/1966 | Norton | 294/74 |
| 4,039,217 | 8/1977 | Bryant | 294/74 |
| 4,052,095 | 10/1977 | Johnson | 294/74 |
| 4,171,840 | 10/1979 | Berzenye | 294/74 |
| 4,239,271 | 12/1980 | Beasley et al. | 294/74 |
| 5,498,047 | 3/1996 | Treuling | 294/74 |
| 5,785,146 | 7/1998 | Palmer | 294/74 |

Primary Examiner—Dean J. Kramer
Attorney, Agent, or Firm—Rising, Ethington, Barnes, Kisselle, Learman & McCulloch, P.C.

[57] ABSTRACT

The webbing sling has a woven nylon webbing member with a top surface, a bottom surface, a first webbing side, a second webbing side, a first eye on one end and a second eye on the other end. A strip of abrasion resistant woven material with a high coefficient of friction is sewn to the top surface of the woven nylon webbing. A liquid urethane is applied to the top surface, the first webbing side and the second webbing side between the first and second eyes. The upper face of the strip of abrasion resistant material is free of urethane. Both eyes are covered by woven abrasion resistant covers that are sewn to the woven nylon webbing and then covered by urethane.

17 Claims, 3 Drawing Sheets

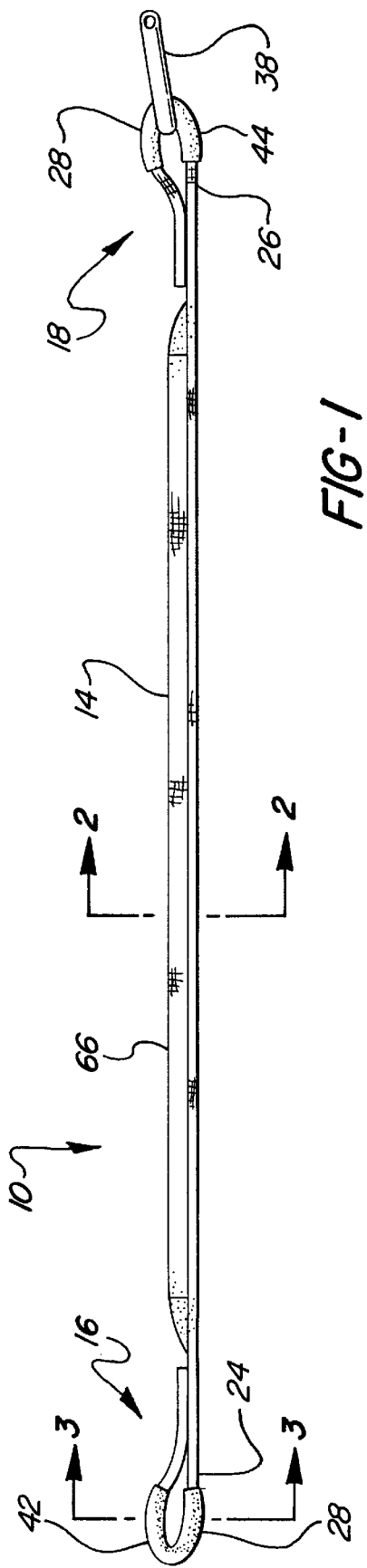
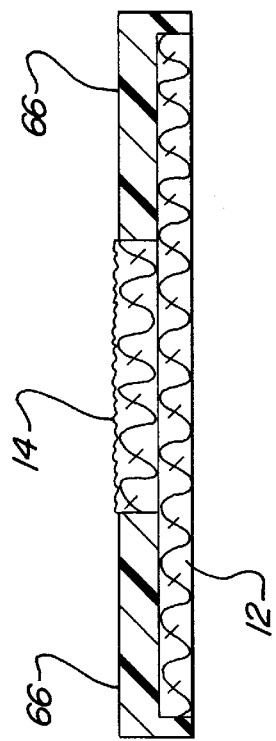
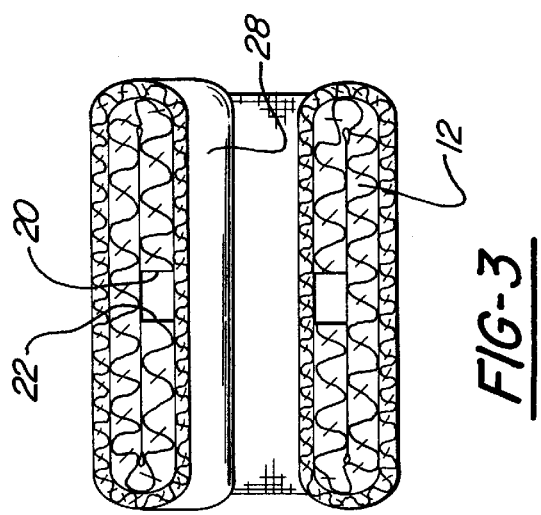

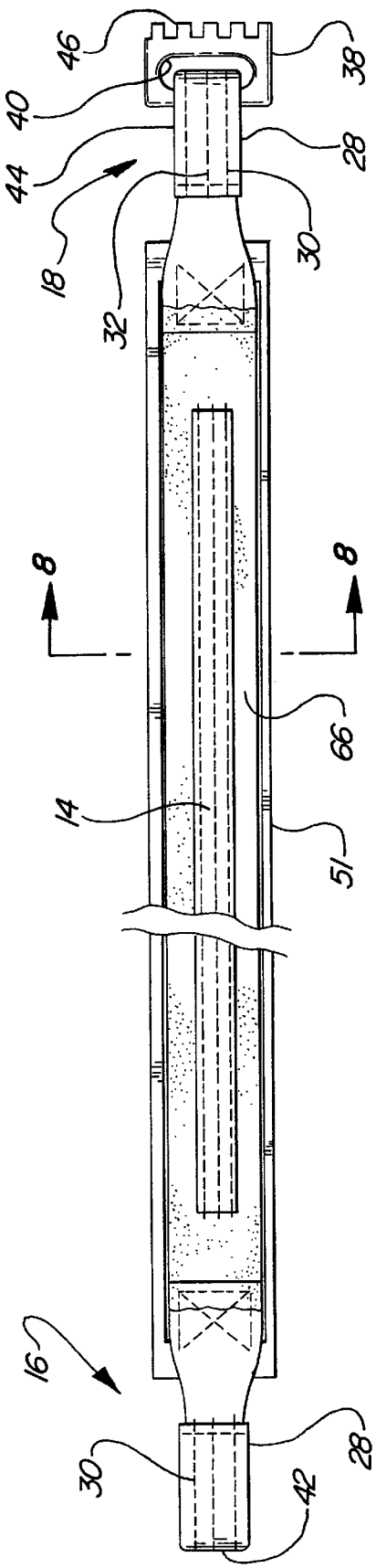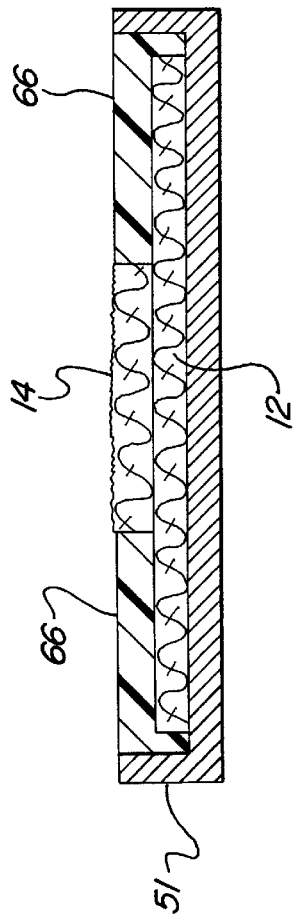
FIG-7
FIG-8

DURABLE SLINGS FOR VEHICLE FRAME TURNOVER MACHINES AND METHOD OF MAKING THE SLINGS

The disclosure incorporates the durable slings for vehicle frame turnover machines and method of making the slings disclosed in provisional patent application Ser. No. 60/091,949, filed Jul. 7, 1998, whose priority is claimed for this application.

TECHNICAL FIELD

This invention relates to a durable nylon webbing sling and more particularly to a durable sling for rotating a vehicle frame 180° about its long axis during vehicle assembly.

BACKGROUND OF THE INVENTION

During the assembly of some vehicles it is common to support a vehicle frame on an assembly line with its bottom side up while the suspension system components are attached to the frame, the axle assemblies are attached to the suspension system components, and other bottom side components are attached. The frame is then rotated 180° to place the frame above the axles and in position to receive additional vehicle components.

Machines to rotate vehicle frames are made by Harnischfeger Corporation in Madison Heights, Mich. These machines includes drums that rotate about two parallel generally horizontal axes. A plurality of slings with an eye on each end have a first eye attached to drums that rotate about one drum axis and a second eye attached to drums that rotate about the other drum axis. The center portion of each sling passes under the vehicle frame. At least two slings are employed to rotate each vehicle frame. Additional slings are added as required depending upon the weight of the frames.

Rotation of the drums on both drum axes to take up the slings will raise a vehicle frame. Rotation of the drums on both drum axes to let out the slings will lower a frame. A frame is generally rotated about its long axis by rolling the slings up about one axis while unrolling the slings from the other drum axis. It is also possible to rotate a frame about the long axis of the frame by rolling the slings up or unrolling the slings from one drum axis while holding the drums on the other drum axis from rotating. However, when the drums on one axis are rotated and the drums on the other axis are held in a fixed position, the slings have to be longer and frame rotation is slower.

The vehicle frames tend to slide on the slings during frame rotation. The frames also tend to swing from side to side when supported by the slings. The sliding and swinging tends to abraid and fray nylon webbing used to make the sling. The fraying and abrading occurs where the slings contact the vehicle frame as well as where the eyes of the slings are attached to the drums. The slings are replaced when there is some abrading and fraying because sling failures cannot be permitted on an assembly line where people are working.

Slings made from unprotected nylon webbing last about two hours on an assembly line running at the rate of 70 units per hour. This short sling life makes operation of the vehicle frame turnover machine expensive.

SUMMARY OF THE INVENTION

An object of the invention is to increase useful life of slings in vehicle frame turnover machines. Another object of the invention is to protect slings from abrading and fraying. A further object of the invention is to provide slings with a wear indicator that provides a visual indication of abrading and fraying.

To increase the life of slings, a strip of blue carboxalated nitrile roughtop is sewn to the surface of the nylon webbing. If the nylon webbing is three inches wide, the blue carboxalated nitrile roughtop that is between about 1½" and 2" wide is sewn to one side of the nylon webbing. The blue carboxalated nitrile roughtop is abrasion resistant and its rough surface tends to hold vehicle frames and reduces sliding contact between the frame and the sling.

The sides of the nylon webbing are folded over and sewn in place to form a tongue on each end of the nylon webbing. The tongues are both folded over and the free end of each of the tongues is sewn to the main body of the nylon webbing to form eyes.

A protective abrasion resistant fabric sleeve woven from nylon filaments is slid over each tongue before the free end of the tongue is sewn in place to form the eyes. The sleeve is sewn to the nylon web tongue along each side of the tongue. Stitches also extend the length of the tubular sleeve in the center of the tongue. Transverse stitches secure each end of the sleeve to the tongue before the eyes are formed. A metal connector is slid over the tongue and the fabric sleeve on each end of the sling. After the metal connectors are in place, each tongue is folded over and the free end of each tongue is sewn to the main body to form eyes as explained above.

The sling is placed in a horizontal mold with the carboxalated nitrile roughtop strip facing upward. A liquid urethane is poured into the mold to encapsulate the nylon webbing and the sides of the carboxalated nitrile roughtop while leaving its outer surface exposed for direct contact with vehicle frames. The eye portion of the sling also receives a urethane coating. The edges of the nylon webbing are encapsulated and increase the width of the sling by about ¼" when the urethane hardens and the sling is removed from the mold. The outside surface of the sling, which faces away from a vehicle frame that is being rotated about its long axis, is not subjected to abrading and fraying and is therefore only partially covered by urethane.

The woven fabric sleeve can be placed on the eye portions of a sling and the eyes can be formed before urethane encapsulation. The eye portions of the sling are then dipped in urethane to obtain a urethane coating. The liquid urethane can also be applied to the webbing before the protective sleeve is placed on each tongue. If the protective sleeve is slid over the tongue after the liquid urethane is applied, urethane is also applied to the protective sleeve after the eyes are formed.

A sling with a urethane coating and the woven protective sleeve described above, extends the life of the sling to ten days when working three shifts per day and rotating seventy vehicle frames per hour. The protective sleeves can also be made from carbon fibers, kavlar fibers or other tough durable fibers.

A plastic pipe made of polyurethane was slid over the tongue to provide eye protection for the sling eyes before the fabric sleeves were employed. With these urethane pipe protectors, a sling had a life of only three days.

Abrading and fraying causes the ends of the fibers making the fabric sleeve to friz forming a thicker more protective shied. When the protective fabric sleeve is worn to the point that the yellow nylon webbing shows, it is time to inspect the sling closely to determine if replacement is required.

BRIEF DESCRIPTION OF THE DRAWINGS

The presently preferred embodiment of the invention is disclosed in the following description and in the accompanying drawings, wherein:

FIG. 1 is a side elevational view of the sling;

FIG. 2 is a sectional view taken along line 2—2 in FIG. 1;

FIG. 3 is a sectional view taken along line 3—3 in FIG. 1;

FIG. 7 is a plan view of the sling in a mold; and

FIG. 8 is a sectional view taken along line 8—8 in FIG. 7.

DESCRIPTION OF THE PREFERRED EMBODIMENT

Figure 4:
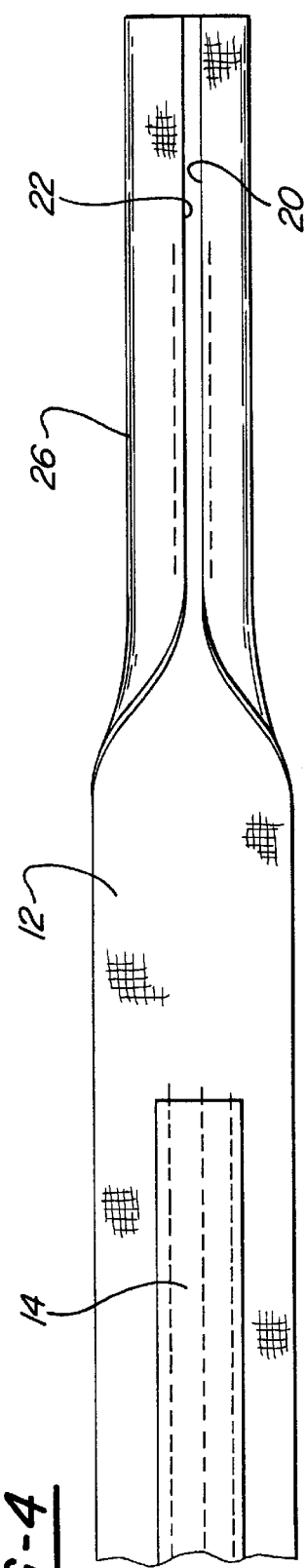
FIG. 4 is an enlarged plan view of the end portion showing the formation of the tongue.
Figure 5:
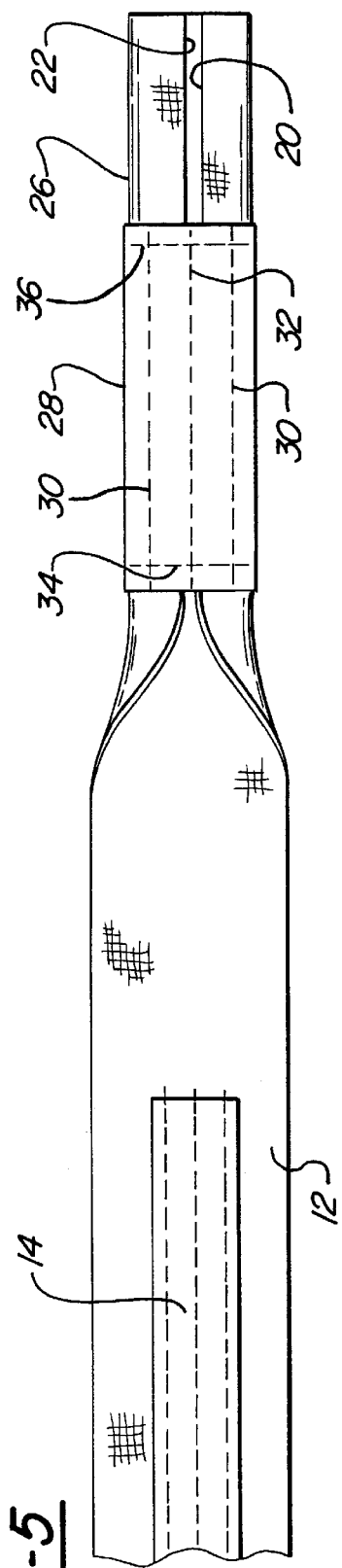
FIG. 5 is a plan view similar to FIG. 4 with the abrasion resistant cover encasing the tongue portion.
Figure 6:
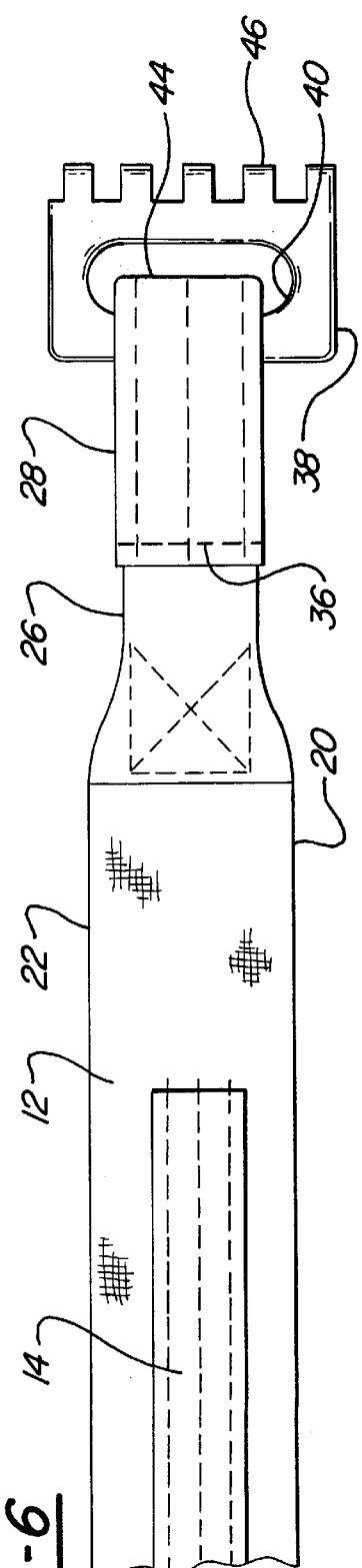
FIG. 6 is a plan view of an eye with the tongue end sewn to the woven nylon webbing and the metal fastener attached.

The sling 10 for a vehicle frame turnover machine are made from a woven nylon webbing 12 that is three inches wide and has a working load limit of 4800 pounds when lifting a load vertically or 9600 pounds when lifting a load as a basket. Depending upon the size and weight of the vehicle frame that is to be turned over, additional slings can be used or the woven webbing 12 can be changed. The nylon webbing 12 specified above is for light and medium duty truck frames. Slings for lighter or heavier vehicle frames and attached components can be made from nylon webbing that has a smaller or larger working load limit rating due to a change in width or a change in the thickness of the webbing. A change in the thickness of nylon webbing 12 may be obtained by adding additional plys of woven nylon during the manufacturing process. The length of the woven webbing 12 depends upon the frame turnover machine that is used and the vehicle frame dimensions. The slings 10 generally have a total length including the eyes of 16 feet.

A strip of blue carboxalated nitrile roughtop 14 is sewn to one side of the webbing 12. This strip of roughtop 14 is between 1½" and 2" wide and about 12 feet long. The roughtop 14 is a three ply material with a rough upper or top surface that has a coefficient of friction of 0.9 when in contact with steel. In addition to the ability of the roughtop 14 to hold vehicle frames and thereby reduce sliding contact with the frames, the roughtop has high abrasion resistance compared to other flexible belting materials.

The ends 16 and 18 of the woven nylon webbing 12 have their sides 20 and 22 folded over and sewn together to form tongues 24 and 26 that are two layers of nylon webbing thick and between 1⅝ and 2 inches wide.

An abrasion resistant woven sleeve 28 is pulled over or slit and wrapped around each of the tongues 24 and 26. This sleeve 28 is woven from nylon filaments which frizz as they become scuffed and worn forming a thicker and more protective shield. Two rows of side stitches 30 and a row of center stitches 32 extend the length of the sleeve 28 and secure the sleeve to each side and the center of each of the tongues 24 and 26. Transverse stitches 34 and 36 close the ends of the tubular sleeve 28.

A metal connector 38 has an aperture 40 that receives the tongue 24 or 26 and the sleeve 28 that encases the tongue. The free end of the tongue 24 is folded back and sewn to the adjacent end of the 3" wide portion of the webbing 12 to form an eye 42 on one end of the webbing. The free end of the tongue 26 is also folded back and sewn to the adjacent end of the 3" wide portion of the webbing 12 to form an eye 44 on the other end of the webbing.

The metal connector 38 has four projections 46 with spaces between them. These projections are interlaced with projections 48 of a second connector and a transverse pivot pin connects the two connectors together. The second connector is secured to a drum of a vehicle frame turnover machine. Each drum of the vehicle frame turnover machine has a similar second connector attached. The first and second connectors 38 and are made from a high strength aluminum such as 6061-T6.

After the eyes 42 and 44 are formed, the sling 10 is placed in a mold 51 for encapsulation in urethane 66. The mold has a flat horizontal floor that supports the sling 10 with the attached belt of blue carboxalated nitrile roughtop 14 facing upward. The sling is secured to the mold floor with a space between the mold walls and the edges of the woven webbing 12. The sides of the mold have upper edges that are slightly below the upper surface of the roughtop 14. The mold is filled with poured urethane 66 and the urethane is allowed to cure. A 95 durometer poured urethane 66 has been found to work well. The cure time is about twenty-four hours. It is preferable to partially fill the mold during a first urethane pour and complete filling the mold during a second urethane pour. Occasionally a third urethane pour is required. A twenty-four hour cure period is provided following each urethane pour. Urethane is also applied to the eyes 42 and 44 by dipping the eyes in urethane and then allowing the urethane to cure. As a result all surfaces of the sling 10, that face toward a vehicle frame that is to be rotated, are covered with urethane with the exception of the frame contacting surface of the blue carboxalated nitrile roughtop 14.

The disclosed embodiment is representative of a presently preferred form of the invention, but is intended to be illustrative rather than definitive thereof. The invention is defined in the claims.

We claim:

1. A webbing sling comprising a woven nylon webbing with a first end, a second end, a top surface, a button surface, a first webbing side and a second webbing side;

a first abrasion resistant cover encasing a first tongue portion adjacent to the first end and sewn to said woven nylon webbing;

a first eye formed by folding the first tongue portion and the first abrasion resistant cover and sewing the first end to said woven nylon webbing;

a second abrasion resistant cover encasing a second tongue portion adjacent to the second end and sewn to said woven nylon webbing;

a second eye formed by folding the second tongue portion and the second abrasion resistant cover and sewing the second end to said woven nylon webbing;

a strip of woven material with an abrasion resistant surface, a first strip side and a second strip side sewn to the top surface of said woven nylon webbing;

a urethane cover that adheres to the top surface of said woven nylon webbing, to the first webbing side of said woven nylon webbing, and to the second webbing side of said woven nylon webbing and that leaves at least a portion of the abrasion resistant surface of said strip of woven material exposed.

2. A webbing sling as set forth in claim 1 wherein the first tongue portion includes a first section with the first webbing side and the second webbing side folded inward toward each other and sewn in place; and wherein the second tongue portion includes a second section with the first webbing side and the second webbing side folded inward toward each other and sewn in place.

3. A webbing sling as set forth in claim 2 wherein the first section of the first tongue portion passes through a first metal connector and the second section of the second tongue portion passes through a second metal connector.

4. A webbing sling as set forth in claim 1 wherein said strip of woven material with an abrasion resistant surface is blue carboxalated nitrile rough top.

5. A webbing sling as set forth in claim 1 wherein the first eye and the second eye are encased in urethane.

6. A webbing sling as set forth in claim 1 wherein the first abrasion resistant cover and the second abrasion resistant cover are tubes.

7. A webbing sling as set forth in claim 6 wherein the first abrasion resistant cover and the second abrasion resistant cover are woven from tough durable fibers.

8. A webbing sling comprising a woven nylon webbing with a top surface, a bottom surface, a first webbing side, a second webbing side, a first eye formed on a first end of the woven nylon webbing and a second eye formed on a second end of the woven nylon webbing;

a strip of blue carboxalated nitrile rough top sewn to the top surface of the woven nylon webbing with a first portion of the top surface of the woven nylon webbing exposed between said strip and the first webbing side and a second portion of the top surface of the woven nylon webbing exposed between said strip and the second webbing side; and a urethane cover applied to the first portion of the top surface and the first webbing side and to the second portion of the top surface and the second webbing side by applying liquid urethane and allowing the urethane to cure.

9. A webbing sling as set forth in claim 8 wherein the cured urethane is translucent.

10. A webbing sling as set forth in claim 8 wherein the urethane is applied to the first webbing side, the second webbing side, the first eye, the second eye and all of the top surface of the woven nylon webbing that remains exposed after the strip of blue carboxalated nitrile rough top is sewn to said top surface.

11. A webbing sling as set forth in claim 10 wherein the strip of blue carboxalated nitrile has a first side, a second side, a first end and a second end that are substantially covered and protected by the urethane.

12. A method of making a webbing sling comprising: cutting a woven nylon webbing to the desired length; forming a first eye on a first end of the woven nylon webbing; forming a second eye on a second end of the woven nylon webbing; sewing a strip of woven material with an abrasion resistant rough top surface to a top surface of the woven nylon webbing; placing a portion of the woven nylon webbing between the first eye and the second eye in a mold with the top surface of the woven nylon webbing facing upward; pouring liquid urethane into the mold and covering all of the webbing sling in the mold but the abrasion resistant rough top surface of the strip of woven material; and curing the liquid urethane.

13. A method of making a webbing sling as set forth in claim 12 including:

covering the first eye with a first abrasion resistant cover and sewing the first abrasion resistant cover to the woven nylon webbing; and covering the second eye with a second abrasion resistant cover and sewing the second abrasion resistant cover to the woven nylon webbing.

14. A method of making a webbing sling as set forth in claim 13 including:

applying a liquid urethane to the first abrasion resistant cover and to the second abrasion resistant cover; and permitting the urethane to cure.

15. A method of making a webbing sling as set forth in claim 12 including:

folding a first edge and a second edge of a first tongue portion of the first eye inward toward each other and sewing the folded first edge and second edge of the first tongue portion of the first eye to the woven nylon webbing; and folding a first edge and a second edge of a second tongue portion of the second eye inward toward each other and sewing the folded first edge and the folded second edge of the second tongue portion of the second eye to the woven nylon webbing.

16. A method of making a webbing sling as set forth in the claim 15 including:

covering the first eye with a first abrasion resistant fabric sleeve and sewing the first abrasion resistant fabric sleeve to first tongue portion of the first eye; and covering the second eye with a second abrasion resistant fabric sleeve and sewing the second abrasion resistant fabric sleeve to the second tongue portion of the second eye.

17. A method of making a webbing sling as set forth in claim 16 including:

applying a first liquid urethane coating to the first abrasion resistant sleeve; and applying a second liquid urethane coating to the second abrasion resistant sleeve.

* * * * *